(12) United States Patent
Vinjamuri et al.

(10) Patent No.: US 9,034,055 B2
(45) Date of Patent: May 19, 2015

(54) HUMAN-MACHINE INTERFACE BASED ON TASK-SPECIFIC TEMPORAL POSTURAL SYNERGIES

(75) Inventors: Ramana Kumar Vinjamuri, Pittsburgh, PA (US); Wei Wang, Sewickley, PA (US); Zhi-Hong Mao, Sewickley, PA (US); Douglas John Weber, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 70 days.

(21) Appl. No.: 13/246,190

(22) Filed: Sep. 27, 2011

(65) Prior Publication Data
US 2012/0078381 A1 Mar. 29, 2012

Related U.S. Application Data

(60) Provisional application No. 61/387,722, filed on Sep. 29, 2010.

(51) Int. Cl.
| | |
|---|---|
| A61F 2/48 | (2006.01) |
| G05B 19/18 | (2006.01) |
| G06F 19/00 | (2011.01) |
| G06E 1/00 | (2006.01) |
| G06E 3/00 | (2006.01) |
| G06F 15/18 | (2006.01) |
| G06G 7/00 | (2006.01) |
| G06F 17/00 | (2006.01) |

(Continued)

(52) U.S. Cl.
CPC ....... *A61B 5/04001* (2013.01); *A61H 2230/085* (2013.01); *A61H 2230/60* (2013.01); *A61F 2002/6827* (2013.01); *A61F 2002/763* (2013.01); *A61H 2230/105* (2013.01); *A61H 2230/08* (2013.01); *A61F 2/68* (2013.01); *A61F 2002/7615* (2013.01); *A61F 2002/764* (2013.01); *A61H 2230/10* (2013.01); *A61H 2230/605* (2013.01); *A61F 2002/7635* (2013.01); *A61B 5/1107* (2013.01); *A61F 2/583* (2013.01); *A61F 2/72* (2013.01); *A61F 2002/704* (2013.01); *A61F 2002/7625* (2013.01); *A61F 2002/7665* (2013.01); *G05B 2219/40195* (2013.01); *A61B 5/6806* (2013.01); *A61B 2505/09* (2013.01); *A61B 2562/046* (2013.01)

(58) Field of Classification Search
CPC ........................... A61F 2/68; A61H 2230/085
USPC ......... 623/24; 700/56, 245; 600/544; 706/22, 706/53; 414/1
See application file for complete search history.

(56) References Cited

U.S. PATENT DOCUMENTS

2006/0135883 A1* 6/2006 Jonsson et al. ................ 600/546
2006/0167564 A1* 7/2006 Flaherty et al. ................ 623/57

(Continued)

*Primary Examiner* — Jacqueline Woznicki
(74) *Attorney, Agent, or Firm* — Kegler Brown Hill & Ritter; James J. Pingor

(57) ABSTRACT

A synergy-based human-machine interface that uses low-dimensional command signals to control a high dimensional virtual, robotic or paralyzed human hand is provided. Temporal postural synergies are extracted from angular velocities of finger joints of five healthy subjects when they perform hand movements that are similar to activities of daily living. Extracted Synergies are used in real-time brain control, where a virtual, robotic or paralyzed human hand is controlled to manipulate virtual or real world objects.

14 Claims, 10 Drawing Sheets

(51) Int. Cl.

| | |
|---|---|
| *G06N 7/00* | (2006.01) |
| *G06N 7/08* | (2006.01) |
| *B25J 1/00* | (2006.01) |
| *B25J 3/00* | (2006.01) |
| *B25J 15/00* | (2006.01) |
| *B25J 19/00* | (2006.01) |
| *A61B 5/04* | (2006.01) |
| *A61B 5/11* | (2006.01) |
| *A61F 2/72* | (2006.01) |
| *A61F 2/68* | (2006.01) |
| *A61F 2/76* | (2006.01) |
| *A61F 2/58* | (2006.01) |
| *A61F 2/70* | (2006.01) |
| *A61B 5/00* | (2006.01) |

(56) References Cited

U.S. PATENT DOCUMENTS

2009/0204558 A1* 8/2009 Weston et al. .................. 706/20
2011/0307079 A1* 12/2011 Oweiss et al. .................. 623/27

* cited by examiner

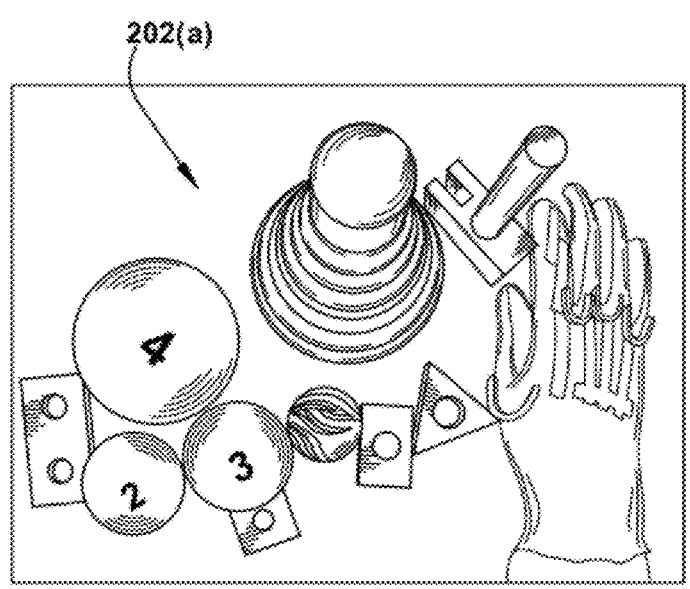
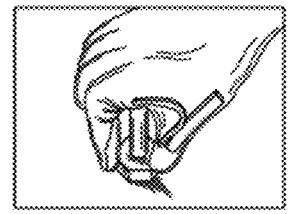
FIG. 2(b)
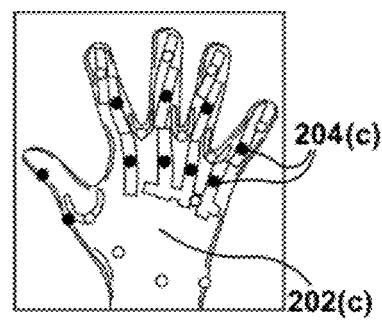
FIG. 2(c)
FIG. 2(a)
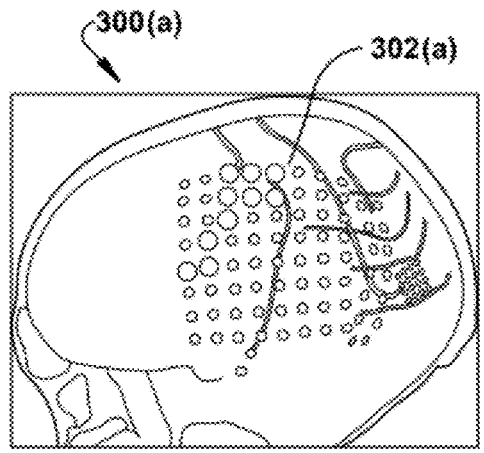
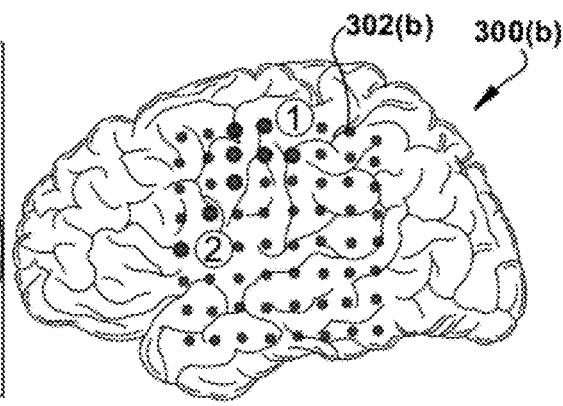
FIG. 3(a)    FIG. 3(b)

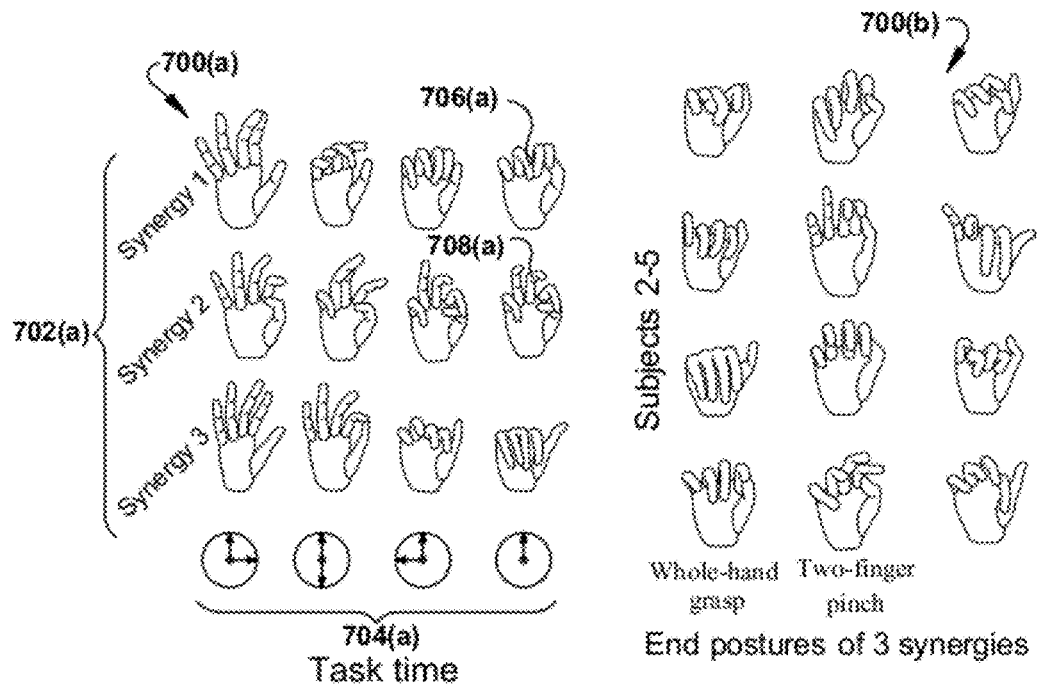
FIG. 7(a) FIG. 7(b)
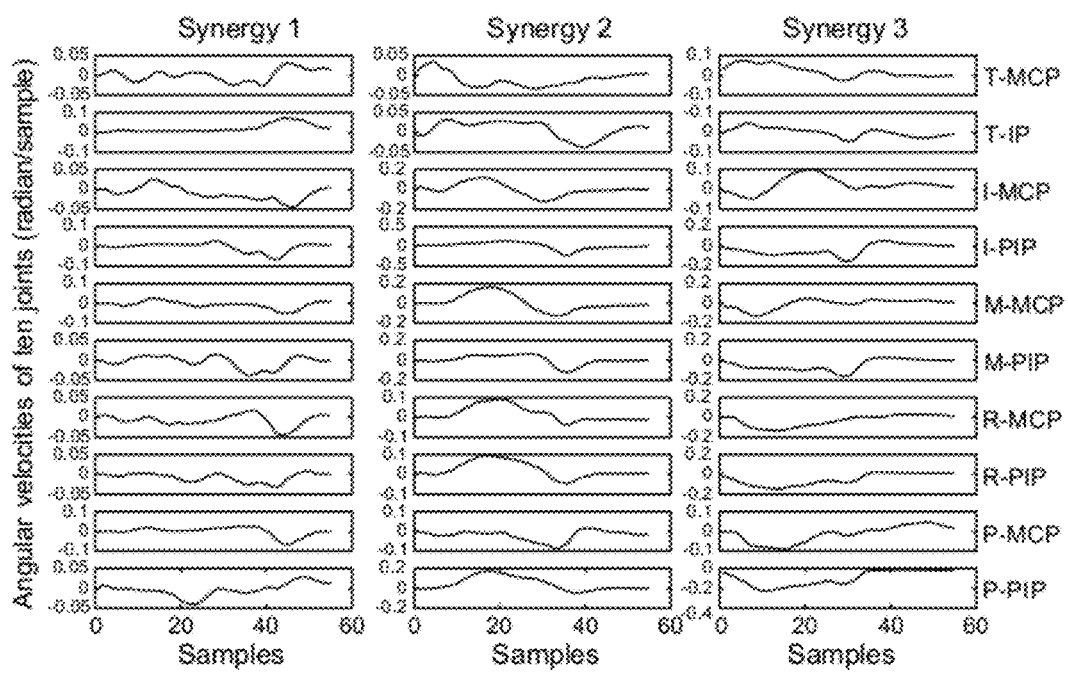
FIG. 8

HUMAN-MACHINE INTERFACE BASED ON TASK-SPECIFIC TEMPORAL POSTURAL SYNERGIES

CROSS-REFERENCE TO RELATED APPLICATIONS

This application claims the benefit of U.S. Provisional Patent application Ser. No. 61/387,722 entitled "HUMAN MACHINE INTERFACE BASED ON TASK-SPECIFIC TEMPORAL POSTURAL SYNERGIES" and filed on Sep. 29, 2010. The entireties of the above-noted applications are incorporated by reference herein.

NOTICE ON GOVERNMENT FUNDING

This invention was made with government support by the National Science Foundation under Cooperative Agreement EEC-0540865, Grant Number 5 UL1 RR024153 from the National Center for Research Resources (NCRR), a component of the National Institutes of Health (NIH) and NIH Roadmap for Medical Research, and a special grant from the Office of the Senior Vice Chancellor for the Health Sciences at University of Pittsburgh. Additional funding support was provided by NIH grants from the NIBIB (1R01EB007749) and NINDS (1R21NS056136) and grant W81XWH-07-1-0716 from the US Army Medical Research and Material Command. The government has certain rights in the invention.

ORIGIN OF THE INVENTION

The innovation disclosed herein is related to a human-machine interface and more specifically, to a human-machine interface that uses low-dimensional command signals to control a high dimensional virtual, robotic or paralyzed human hand.

BACKGROUND

In the United States alone, there are over 200,000 people living with a chronic spinal cord injury (SCI). People with chronic SCI have impaired motor functions that limit their ability to perform activities of daily living, such as grasping and manipulating objects. A recent survey of 681 people with tetraplegia, also known as quadriplegia, demonstrated that for over 45%, regaining arm and hand function would improve their quality of life significantly. Improving impaired motor function can enable increased social participation and greater independence. At the present, physical therapy and biofeedback aim to augment function in residual muscles after chronic SCI. For muscles with complete loss of descending drive, however, these therapies are ineffective. Functional electrical stimulation (FES) systems have had limited success in restoring functionally important grasps for some individuals with tetraplegia. However, while sophisticated FES systems have been developed, one of the main challenges for FES systems is to obtain multiple independent control signals that allow stimulation of muscles in a coordinated fashion in order to generate smooth and natural hand movements.

SUMMARY

The following presents a simplified summary in order to provide a basic understanding of some aspects of the innovation. This summary is not an extensive overview of the innovation. It is not intended to identify key/critical elements or to delineate the scope of the innovation. Its sole purpose is to present some concepts of the innovation in a simplified form as a prelude to the more detailed description that is presented later.

The innovation disclosed and claimed herein, in one aspect thereof comprises a method of controlling the movement of an extremity. The method includes performing a plurality of tasks and extracting a plurality of temporal postural synergies from angular velocities of a plurality of joints based on the performance of the plurality of tasks. The method further includes receiving a plurality of control signals from a subject with a neurological disorder and controlling the plurality of temporal postural synergies with the plurality of control signals. The plurality of control signals are convolved with a plurality of finite impulse filters and an output response from the plurality of finite impulse filters are added to obtain a resultant angular velocity profile. The resultant angular velocity profile is integrated to obtain a joint position used to control movement of the extremity.

The innovation disclosed and claimed herein, in another aspect thereof comprises a human-machine interface (HMI) system that includes an extraction component that extracts a plurality of kinematic synergies via a movement recording component, wherein the movement recording component includes a plurality of joints, a transformation component that transforms the plurality of kinematic synergies into a plurality of temporal postural synergies, a receiving component that receives control signals from a subject having neurological disorders, a convolving component that convolves the control signals with a plurality of kinematic synergies that are essentially finite impulse response (FIR) filters, a combination component that combines output responses from the convolving component that obtains a resultant angular velocity profile, and a calculating component that calculates movement of an extremity based on the resultant angular velocity profile.

BRIEF DESCRIPTION OF THE DRAWINGS

FIG. 2 is an example diagram showing objects and equipment used in the synergy-based BMI in accordance with the innovation.

FIG. 3 is an example of a head X-ray and a 3-D reconstruction respectively of a brain both illustrating the placement of an electrode array in accordance with the innovation.

FIG. 7 is an example illustration of resulting synchronous postural synergies in accordance with the innovation.

FIG. 8 is an example illustration of waveform graphs showing resulting asynchronous synergies in accordance with the innovation.

DETAILED DESCRIPTION

Figure 1A:
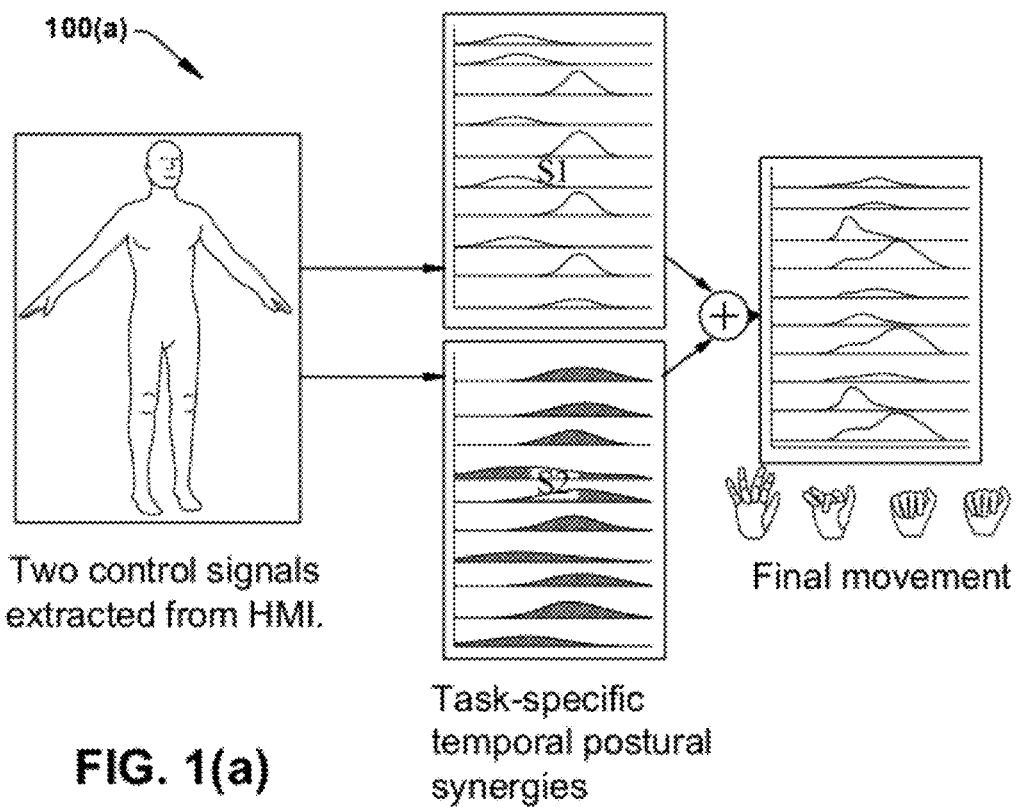
FIG. 1(a) is an example block type schematic diagram of a synergy-based Human-Machine Interface (HMI) system in accordance with the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As will be described in more detail below, disclosed herein is a synergy-based human-machine interface (HMI) system 100($a$), shown in FIG. 1($a$) that uses low-dimensional command signals to control a high dimensional virtual hand. One embodiment of an HMI 100($a$) is a brain machine interface (BMI) 100($b$), shown in FIG. 1($b$). It is to be appreciated that other human machine interfaces, such as a muscular machine interface, can be used with the innovation disclosed herein. Thus, the embodiment described herein and illustrated in the figures is for illustrative purposes only and is not intended to limit the scope of the innovation. Temporal postural synergies are extracted from angular velocities of finger joints of five healthy subjects when the subjects perform hand movements similar to activities of daily living. Two synergies inspired from the extracted synergies, a two-finger pinch and a whole-hand grasp, are used in real-time brain control, where a virtual hand with 10 degrees of freedom is controlled to grasp or pinch virtual objects. These two synergies, controlled by electrocorticographic (ECoG) signals recorded from two electrodes of an electrode array that spans motor and speech areas of an individual with intractable epilepsy, demonstrate a closed loop control of a synergy-based brain-machine interface.

Synergies have been considered as common movement primitives that can be generalized for several kinds of movements. In the innovation disclosed herein, however, it was determined that synergies may also be task specific. Thus, how the synergies are extracted depends on the context of end user application.

BMI's provide a viable and powerful solution for the above described user-control problem by accessing and decoding the native motor control signals embedded in the activity of neurons in sensorimotor regions of the brain. BMI's have demonstrated accurate and reliable one and 2-D computer cursor control in human studies. It is to be appreciated that direct brain control of a 4-D robotic arm, allowing a monkey to feed itself via "brain-control" has been demonstrated. One of the major challenges is extending this technology to control high-dimensional systems, for example, controlling a human hand, which has over 27 degrees of freedom (DoF).

Movement planning functions in the brain are hypothesized to occur in a low-dimensional subspace of movements called movement primitives often referred to as synergies. Synergies enable control of multiple DoF of movement with fewer control signals. For example, it was previously demonstrated that 100 hand grasping movements can be reconstructed with 10-15 active DoF using weighted linear combinations of six synergies. Further, it is to be appreciated that two synergies can account for 60% of tasks similar to activities of daily living. Also, in local ensembles of M1 neurons recorded from small intracortical arrays in macaques contained sufficient information to reconstruct 25 joint angles of arm, wrist, and hand during reach and grasp tasks with 10 active DoF. This type of synergy-based control means that hundreds of hand postures can be achieved with a limited number of synergies.

Combining the advantages of BMI and the concept of synergies, demonstrates the control of a 10 DoF virtual hand using two neural control signals in a synergy-based BMI 100($b$), as illustrated in FIG. 1($b$) and described further below. Although specific tasks are described herein, such as a whole hand grasp and a two finger pinch, it is to be appreciated that the innovation may be applied to other types of daily living type tasks. For purposes of simplicity, however, in the embodiment described herein and shown in the figures, the tasks will relate to the whole-hand grasp and the two finger pinch. Thus, the embodiment described herein and shown in the figures is for illustrative purposes only and is not intended to limit the scope of the invention. For example, if the task intended is typing then there will be a different set of task specific synergies. If the task intended is moving the arm, then arm joints will be included in the synergies.

Demonstration of this synergy-based BMI is twofold. First, temporal postural synergies $s^1$, $s^2$ are extracted from five healthy subjects performing grasping tasks similar to activities of daily living, using two methods: a Singular Value Decomposition (SVD) and a Gradient Descent Method (GDM). Although, the SVD method and the GDM are disclosed herein, it is to be appreciated that other methods such as but not limited to, other linear and nonlinear dimensionality reduction methods can also be used to extract the synergies. Second, the extracted synergies $s^1$, $s^2$ are used in the development of a real-time electrocorticogoraphy (ECoG) based BMI and tested in one subject with electrodes implanted intracranially for monitoring epileptic seizures.

The following description illustrates a Convolutive Mixtures Model for Generation of Hand Movement. Still referring to FIG. 1($b$), an illustration of how brain-controlled synergies combine to form movement is shown. Grasping hand movement is achieved by a weighted linear combination $(w_1 s^1 + w_2 s^2)$ of two synergies, where $w_1 = 0.5$ and $w_2 = 0.5$ represent the weights extracted from neural recordings. The weighted combination of two time-varying synergies $s^1$, $s^2$ leads to the formation of a hand movement profile. Specifically, two neural signals control two distinct synergies $s^1$, $s^2$ to achieve a grasping hand movement using a weighted linear combination $(w_1 s^1 + s^2 w_2)$ of two synergies, where $w_1$ and $w_2$ represent weights extracted from brain signals. Each row of a synergy corresponds to the angular velocity profile of a finger joint. For example, the first synergy represents the synchronous large movement of first joint and medium movement of the second joint followed by a small movement of the third joint. In this example, $s^1$ and $s^2$ form a weighted ($w_1 = w_2 = 0.5$) combination resulting in the aggregate movement (black) in the reconstructed joint angular velocity graph 102. For illustration purposes, only three of ten joints of the hand are shown in the synergies and the reconstructed movement. FIG. 1($b$) also shows the hand postures 104 of the reconstructed movement across time.

Figure 1B:
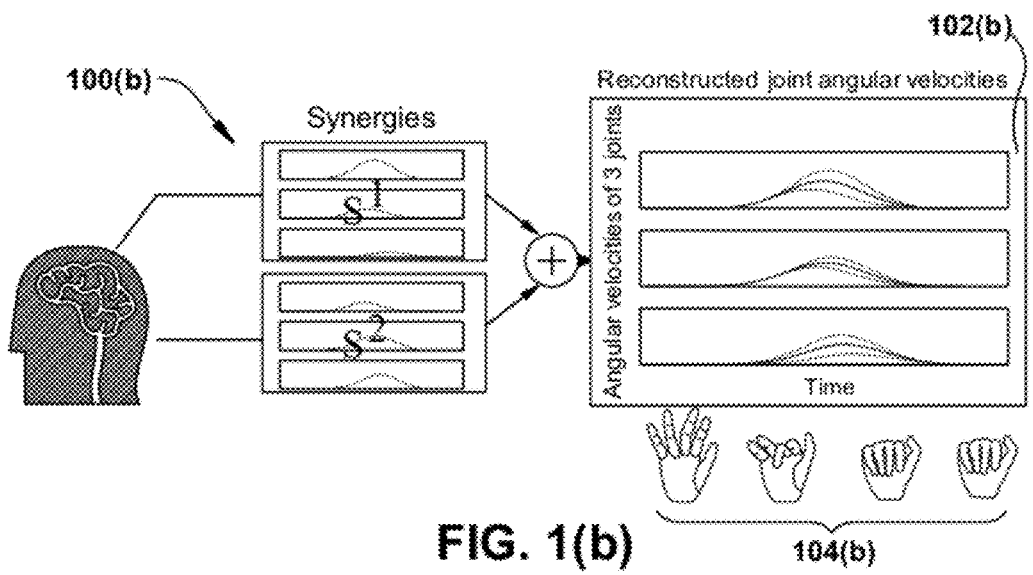
FIG. 1(b) is an example block type schematic diagram of a synergy-based Brain-Machine Interface (BMI) in accordance with the innovation.

Still referring to FIG. 1(b), it is possible that synergies may be recruited multiple times by the brain to achieve certain movements. This is accounted for in a convolutive mixtures model, which is a hypothetical model that presents the synergy decomposition problem in solvable form. A mathematical model, generalized for m synergies that can be reused $K_j$ times can be numerically represented as Formula 1(a) or 1(b) below:

$$v(t) = \sum_{j=1}^{m} \sum_{k=1}^{K_j} c_{jk} s^j(t - t_{jk}) \quad \text{Formula 1(a)}$$

or $$v(t) = \sum_{j=1}^{m} \sum_{k=1}^{K_j} c_{jk} s_i^j(t - t_{jk}), \, i = 1, \ldots, n. \quad \text{Formula 1(b)}$$

In the above equations, v(t) denotes $[v_1(t), \ldots, v_n(t)]'$, where ' represents transpose, $v_i(t)(i=1, \ldots, n)$ represents an angular velocity of the i-th joint of the hand at time t, and n is the total number of the considered joints of the hand; a single kinematic synergy is denoted $s_j(t) \equiv [s^j_1(t), \ldots, s^j_n(t)]'$, where j ranges from 1 to m and m is the total number of synergies; $K_j$ is the number of repeats of the j-th synergy used in v(t), and $c_{j\,k}$ and $t_{j\,k}$ represent the amplitude coefficient and time shift, respectively, of the k-th repeat of the synergy $s^j(\bullet)$. The example shown in FIG. 1(b) can be expressed using the above equations with n=3 joints, m=2 synergies, $K_j$=1 (both synergies used once), $c_{jk}$=0.5 for weights $w_1$=$w_2$=0.5, and $s^j(\bullet)$ as a matrix with three rows and as many columns as there are time samples. The reconstructed angular velocities v(t) are the same dimension as $s^j(\bullet)$.

Figure 4A:
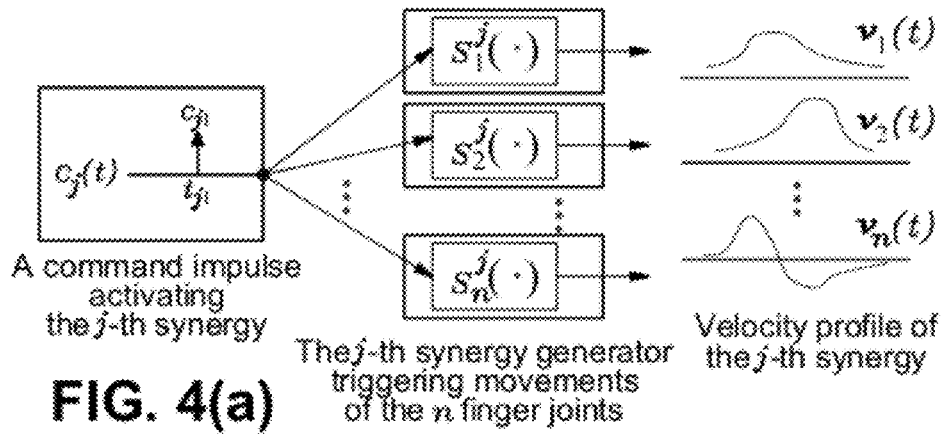
FIGS. 4(a)-(d) are example block diagrams of a hypothesized model for the generation of hand movement in accordance with the innovation.
Figure 4B:
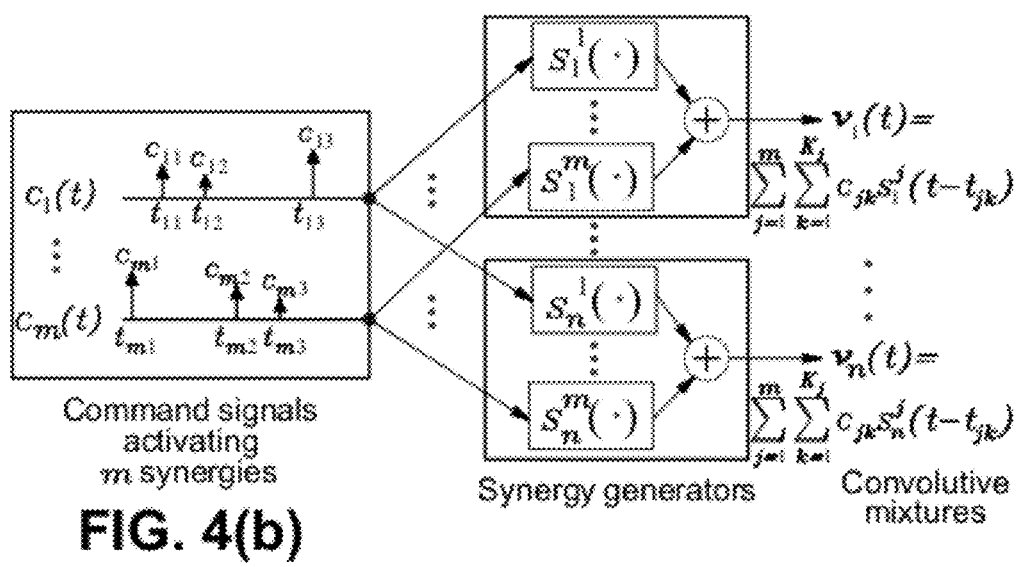
Figure 4C:
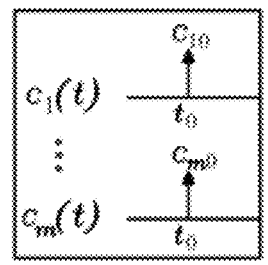

The synergy-based movement generation can be interpreted by the convolutive-mixture model. Specifically, referring to FIGS. 4(a) and (b), the angular velocities $v_i$ of finger joints can be modeled as convolutive mixtures of neural command signals represented by impulse trains. This process can be viewed as the activation of a synergy and is similar to the production of impulse responses of a set of filters, each of which triggers the movement of a specific finger joint. Based on the above model, when the j-th synergy generator is activated by a command signal $c_j(t)$ containing a train of impulses with amplitudes $c_{j\,k}$ at times $t_{jk}$, k=1, \ldots, $K_j$, an angular-velocity profile of the finger joints becomes:

$$v(t) = (c_j * s^j)(t) = \sum_{k=1}^{K_j} c_{jk} s^j(t - t_{jk}) \quad \text{Formula 2}$$

where * represents convolution. When more than one synergy is considered (see FIG. 4(b)), the convolutive mixture model can then be expressed by either Formula (1a) or (1b). Specifically, a movement profile of the hand can be modeled as the convoluted mixtures expressed by either Formula (1a) or (1b) of command impulses passing through the corresponding filters or synergy generators.

Referring to FIGS. 2(a)-2(c), a first experiment is performed with five healthy subjects (subjects 1-5), male and female ages 27-35 years, with no known neurological disorders. The subjects are tested in a set of behavioral tasks that are based on activities of daily living. All five participants wore a cyber glove 202(c) during the experiment, as shown in FIG. 2(c). The cyber glove 202(c) is equipped with 22 sensors that measures an angle of each finger joint, including the distal interphalangeal (DIP), proximal interphalangeal (PIP) and metacarpophalangeal (MCP) joint angles. For this experiment, however, only ten of the sensors (MCP and PIP joints), as indicated by the dark circles 204(c) in FIG. 2(c) were analyzed. As shown in FIG. 2(a), multiple wooden and plastic objects 202(a) of different shapes (e.g. spheres, circular discs, rectangles, pentagons, nuts, and bolts) having dimensions ranging from 1.5 cm to 11.8 cm were presented to the subjects based on two criteria. First, objects of the same type but different sizes were included. Second, objects having different shapes were chosen to isolate proximal and metacarpal joints. A typical experiment consisted of 28 tasks corresponding to 28 objects. In each task, the subject was seated comfortably and rested their hand at corner of a table. When prompted, the subject reached and grasped the object visibly placed 40 cm away on the table, as shown in FIG. 2(b). Each trial lasted for 1 second. The subjects completed 10 trials for each task (object) type. Rest breaks of approximately 2-3 minutes were incorporated between the tasks. The beginning and the end of the task were indicated by computer-generated beeps. Although the grasping times differed slightly from object to object, all of the subjects were able to grasp the objects within 0.86 seconds. This time window of 0.86 seconds was used for further analysis.

In a second experiment, one subject with intractable epilepsy was used to demonstrate real-time control of the synergy-based BMI. As part of the standard clinical procedure for epilepsy monitoring, an 8×8 intracranial electrocorticographic (ECoG) electrode array was implanted to help with the planning of surgical treatment for intractable epilepsy. The electrode array includes 64 disc electrodes, 3 mm in diameter with a 10 mm inter-electrode distance, embedded in a silastic sheet. FIG. 3(a) is a head X-ray 300(a) of the subject with the 8×8 ECoG electrode array 302(a) covering the parietal lobe, temporal lobe and posterior portion of the frontal lobe of the left hemisphere. The colored dots indicate areas related to hand movement (red) or speech (green) as determined by cortical stimulation mapping for localization of eloquent (e.g., motor and language) areas of the cortex. Because multiple electrodes responded to hand movement and vocalization, the electrodes showing the greatest difference in time-averaged spectral power compared to baseline spectra during rest were selected for brain control. The selection of electrodes is an active area of research in neuroscience. Automatic detection of favorable electrodes can be used in conjunction with a synergy-based HMI.

FIG. 3(b) shows the electrode grid location 302(b) projected on a standard 3-D brain model 300(b) showing the electrodes selected for brain control. Neural signals recorded using a neural recording system were band-pass filtered between 0.1 and 200 Hz and digitized at a sampling rate of 1200 Hz. These digitized ECoG signals were sent to a custom-built high-performance computer 502, such as but not limited to a BCI2000 (see FIG. 5), running a general purpose software package for real-time BMI studies. The recorded signals were transformed into a frequency domain using an autoregressive model (e.g. maximum entropy method) of order 18, with a bin width of 10 Hz using a sliding window of 300 ms. Spectral power for the two selected electrodes was averaged over the high frequency (e.g. 75-115 Hz) band. Spectral estimates were performed at 30 Hz and fed into a real-time model as control signals. The control signals may be comprised of invasive or non-invasive brain (neural) signals or muscular signals generated from neck muscles, shoulder muscles, etc., Further, the control signals may be signals detected by peripheral sensors that detect the parameters like limb movement, sound or temperature. For example, a peripheral sensor may track a movement of an eye (eye tracker), the movement of the head (head tracker). A peripheral sensor may detect the clicking of teeth (tooth click sensor).

Both synchronous and asynchronous synergies are extracted from the subjects as described below. As mentioned above, the convolutive mixtures model is a hypothetical model that presents the synergy decomposition problem in a solvable form. The neural representation of synergies and the existence of synergies are an ongoing field of research. Nevertheless, the above model assists in formulating the problem of using synergies in the field of neural prostheses and robotics. It is unknown if the synergies are recruited synchronously or asynchronously by human beings during natural grasping movements. Therefore, both synchronous and asynchronous synergy models are disclosed herein. It should be noted that these special cases also help in modular reduction to decrease the computational burden of this complex synergy decomposition problem.

An assumption is that the synergies combine instantaneously in order to generate the grasping movements performed by the subjects in the first experiment. FIG. 4 (c) is an illustration where a reach and grasp movement is achieved as a weighted sum of synchronous (having the same onset time) synergies. Thus, as a special case of the convolutive mixtures model, the angular-velocity profile of a movement can be assumed to be a weighted summation of synchronous synergies as expressed in the following:

$$v(t) = \sum_{j=1}^{m} c_{j0} s^j (t - t_0)$$ Formula (3)

where the impulses $c_j(t)$, $j=1, \ldots, m$, occur at the same time $t_0$ but may have different amplitudes $c_{j0}$. As mentioned above, the Singular Value Decomposition (SVD) method is used to extract synchronous synergies.

Figure 4D:
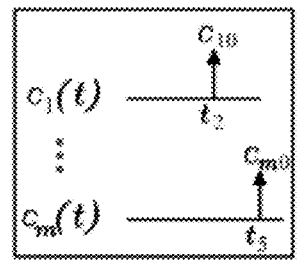

FIG. 4(d) illustrates that a reach and grasp movement is achieved as a weighted sum of asynchronous (having different onset times) synergies. Because asynchronous synergies may not combine instantaneously or may combine at different times, the gradient descent method based on a recursive minimization of the reconstruction error is used to extract the synergies. Thus, the following formula is obtained by reducing the convolutive mixtures model of Formula (1a):

$$v_p(t) = \sum_{j=1}^{m} c_{jp} s^j (t - t_{jp})$$ Formula (4)

where subscript p denotes a particular task in which the subject reached and grasped a particular object. Note that the weights of synergies $c_{jp}$ and time shifts of the synergies $t_{jp}$ are specific to the task, but the synergies $s^j(\cdot)$ are the same across all the tasks. Joint angular velocities, $v_p(t)$ are calculated from recorded joint angles. Then a recursive minimization of reconstruction error algorithm is used to find the weights $c_{jp}$, and time-shifts $t_{jp}$ of the synergies as well as the synergies $s^j(\cdot)$ themselves.

The following is a description of the steepest descent method using a recursive minimization of reconstruction error to find the minimum error. In this method, averaged angular velocities $v_p(t)$ across each trial is obtained for each object. One such angular velocity profile has ten rows corresponding to the ten joints (MCP and PIP) of five fingers. The number of columns is equal to the number of samples. These angular velocity profiles are then used as inputs to the gradient descent method, described below. For each subject, optimization was performed in eight cases in which an increasing number of synergies, 1 to 8, are considered. The reconstruction error is given by:

$$E = \sum_{p=1}^{P} E_p^2$$ Formula (5a)

$$E_p^2 = \sum_{t=1}^{T_p} \left\| v_p(t) - \sum_{j=1}^{m} c_{jp} s^j(t - t_{jp}) \right\|^2$$ Formula (5b)

where $\|\ \|$ is the Euclidian norm, E is the total error, $E_p$ refers to the error per task, $T_p$ is duration of a task and P refers to the total number of tasks.

The steepest descent method having a constant step size is an optimization algorithm used to minimize the error. For each subject and for each number of synergies (m), the algorithm was run multiple times, starting from different initial values of the synergies to avoid local minima. The stopping criterion of the algorithm was chosen to be approximately 2000 iterations, as at this point there was no appreciable decrease in the total error E.

The algorithm can be broken down to three major acts. 1) Find optimal synergy shifts: Compute the sum of scalar products of the $p^{th}$ task and $j^{th}$ synergy shifted by time t or the scalar product of the cross-correlation at delay t, for all possible delays. Select the synergy and delay $t_{jp}$ with the highest cross-correlation. Subtract from the data the selected synergy (after scaling and time shifting). Repeat this for remaining synergies. This completes one task/object. Repeat the same for all remaining tasks. 2) Update the weights: For each task, given the synergies and delays $t_{jp}$, update the weights $c_{jp}$ using the gradient descent method $$\Delta c_p = -\mu_c \nabla_{c_p} E_p^2$$

where $c_p$ denotes $[c_{1p}, \ldots, c_{mp}]'$, where ' represents transpose. 3) Update the synergies: Given optimal shifts and updated weights, update the synergy elements $s_{j\tau} = s^j(\tau)$ by the gradient descent method.

$$\Delta s_{j\tau} = -\mu_s \nabla_{s_{j\tau}} E^2$$

After these acts are performed, the error is calculated and the above acts are repeated until the lowest possible error is achieved. The number of synergies is predicted by the minimum number of synergies needed to yield the lowest possible reconstruction error.

Figure 5:
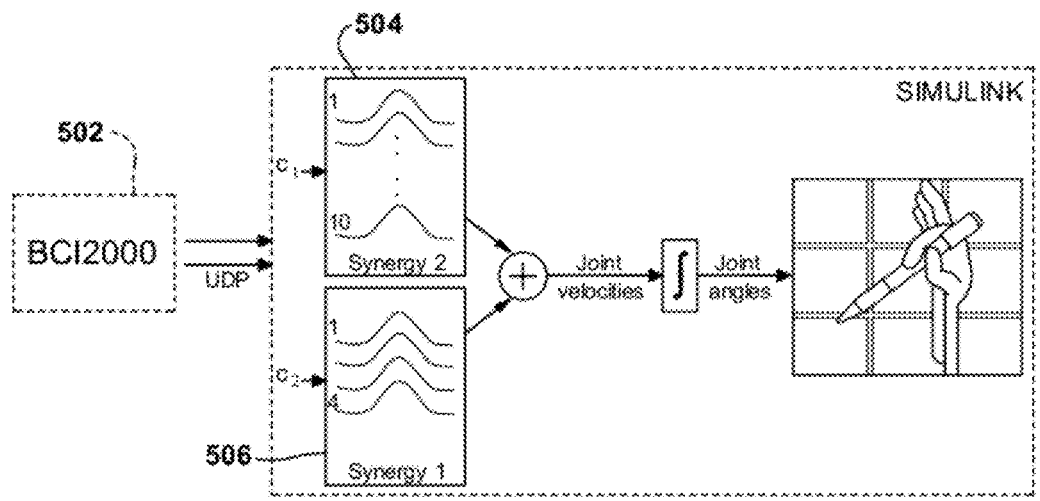
FIG. 5 is an example real-time model in accordance with the innovation.

An example of the development of a real-time Hand Control Model is described with reference to FIG. 5. FIG. 5 is an example block diagram illustrating the real-time Hand Control Model 500. The model 500 receives two neural signals $c_1$, $c_2$ that control two synergies, synergy 2 and synergy 1 respectively. These neural signals $C_1$, $c_2$ are computed as the average spectral power of the high frequency (75-115 Hz) band from two selected electrodes. It has been observed that the high frequency spectral power of the ECoG and local field potential signals recorded from the motor cortex contains motor related information. During the brain-control task, the subject was asked to modulate their neural activity in order to control the synergies to grasp a ball, pinch a pen, or be idle in the virtual world. The two synergies in the model correspond to a two-finger pinch, synergy 1, and a whole-hand grasp, synergy 2. These two synergies are inspired by the synergies extracted from the first part of the study. Each synergy, synergy 1, synergy 2, was modeled as a bank of Gaussian filters 504, 506. A Gaussian filter is a finite impulse response (FIR) filter that has a Gaussian bell shaped impulse response. Each filter corresponds to a single finger joint. As such, the two-finger pinch synergy, synergy 2, had only four Gaussian filters 502 that corresponded to four joints (two per finger) of the index finger and the thumb. Similarly, the whole-hand grasp synergy, synergy 1, has ten Gaussian filters 506 that correspond to ten joints of the four fingers and the thumb. The neural signals $c_1$, $c_2$ were convolved with the Gaussian FIR filters 504, 506 to generate a response. Output form the two synergies are added to provide the resultant angular velocity profile, which when integrated results in joint positions used to control the virtual hand 202 (c). Using (1b) and (2), this can be represented as:

$$v_i(t) = \sum_{m=1}^{2} s_i^j(t) * \max\{P_j(t) - P_{th}, 0\} \quad \text{Formula (6)}$$

where $P_j(t)$ represents the spectral power of the neural signal and $P_{th}$ is a power threshold. The high-gamma band power (after being subtracted off the threshold) continuously convolves with the synergies to result in angular velocities. Unlike the convolutive mixtures model that uses discrete impulses to control synergies, the real-time model uses continuous control signals (i.e., high-gamma band power). This is because the command signals are high-gamma band powers of the signals recorded from the ECoG electrodes, which reflect the ensemble neuronal activity and not single neuron activities. As Formula (6) demonstrates, when the task spectral power is below the power threshold, the command signal controlling a synergy is null resulting in zero joint angular velocity. On the other hand, when the task spectral power is above the power threshold, the joint angular velocity is proportional to the power spectral difference. The resultant angular velocities are then integrated to obtain the joint positions that controlled the virtual hand. As mentioned above, the 10 degrees of freedom of the virtual hand correspond to the five MCP joints and five PIP joints of thumb and four fingers.

Figure 6:
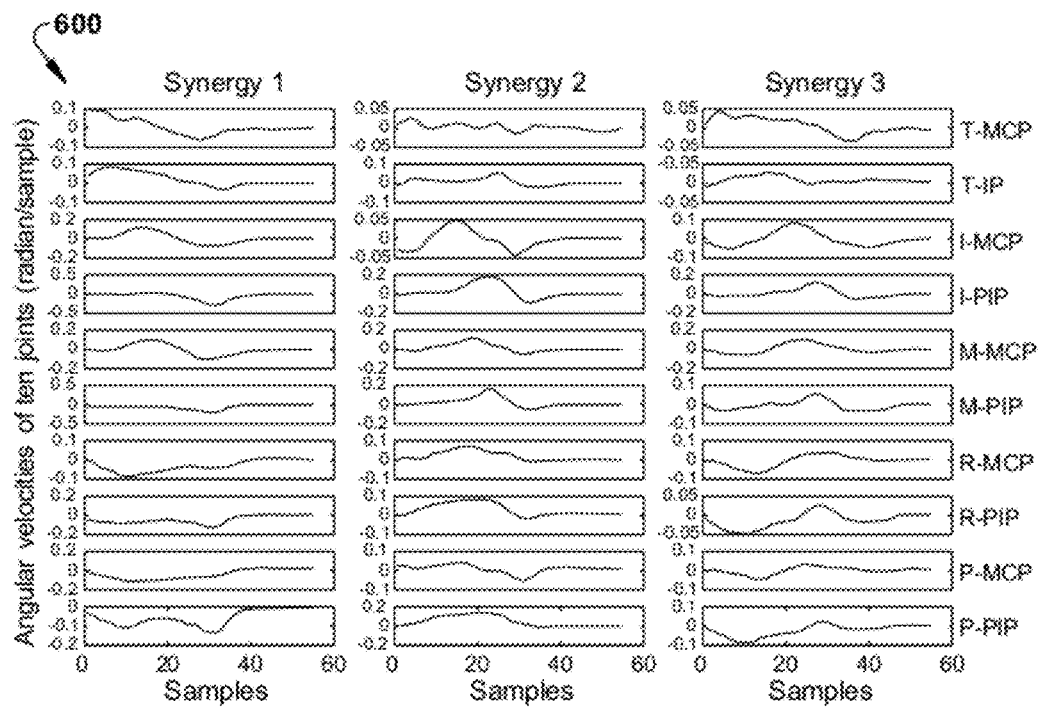
FIG. 6 is an example illustration of waveform graphs showing resulting synchronous synergies in accordance with the innovation.

As mentioned above, the synchronous synergies were obtained using the SVD method. Synergy waveforms 600 of the resulting kinematic synergies for subject 1 are shown in FIG. 6. Each synergy is about 0.86 seconds in length (55 samples at 64 Hz). The abbreviations for FIG. 6 are as follows: T—thumb; I—index finger; M—middle finger; R—ring finger; P—pinky finger; MCP—metacarpophalangeal joint; IP—interphalangeal joint; PIP—proximal interphalangeal joint.

The first three synergies, synergy 1, synergy 2, synergy 3, selected are the first three eigenvectors, which corresponded to the top three eigenvalues. These three synergies cumulatively account for 90% of the variance of all hand postures during the 28 grasping tasks. Note that the synergies, synergy 1, synergy 2, synergy 3, are in the space of angular velocities. Given the initial "open" hand posture, joint velocities are integrated to produce joint positions of intermediate postures. These are referred to as temporal postural synergies, as they preserve both the temporal and the postural information contained in the synergies.

A similarity index (SI) (on a scale of 0-1, where 0 represents a minimum similarity and 1 represents a maximum similarity) based on the normalized inner product between the joint position vector of the obtained posture and that of an ideal whole-hand grasp or an ideal two-finger pinch is calculated. The ideal whole-hand and two-finger pinch grasps are determined by the joint angles of the virtual hand, shown in FIGS. 7 and 9, when 1) all the fingers and the thumb are flexed during a whole-hand grasp, and 2) the thumb and the index finger are flexed during a two-finger pinch. The similarity index measures how similar an end posture of particular synergy is to either a whole-hand grasp or a two-finger pinch.

The temporal evolution of postural synergies 700(a) for subject 1 is shown in FIG. 7(a). Each row corresponds to a temporal profile of one synergy. Each posture 702(a) is a snapshot taken at discrete time steps 704(a) of 25%, 50%, 75%, and 100% of a task time. The synergies are arranged in the order of their significance, with the first row (synergy 1) being the most significant, the middle row (synergy 2) being less significant, and the last row (synergy 3) being the least significant. The end posture 706(a) of synergy 1 corresponds to a whole-hand grasp (SI=0.99) and an end posture 708(a) of synergy 2 corresponds to a two finger pinch (SI=0.99).

FIG. 7(b) shows the postural synergies 700(b) of subjects 2-5. Each row corresponds to the end postures of three significant synergies for each subject. The first and second columns correspond to whole-hand grasp (SIs=0.99, 0.95, 0.94, 0.98 for subjects 2-5, respectively) and two-finger pinch synergies (SIs=0.94, 0.98, 0.95, 0.90) observed across the subjects.

As mentioned above, asynchronous synergies 800 were obtained using the steepest descent method. Synergy waveforms 800 of the resulting kinematic synergies for subject 1 are shown in FIG. 8. Each synergy is 0.86 s in length (55 samples at 64 Hz). The abbreviations for FIG. 8 are as follows: T—thumb; I—index finger; M—middle finger; R—ring finger; P—pinky finger; MCP—metacarpophalangeal joint; IP—interphalangeal joint; PIP—proximal interphalangeal joint. In contrast to the synchronous synergies derived using the SVD method, the asynchronous synergies are not ranked in order of significance. Using the methods described above, the asynchronous kinematic synergies are transformed to temporal postural synergies.

Figure 9A:
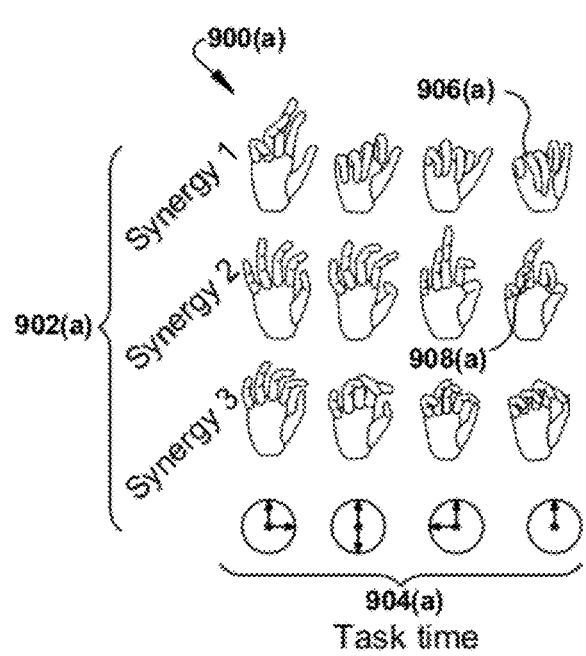
FIG. 9 is an example illustration of resulting asynchronous postural synergies in accordance with the innovation.
Figure 9B:
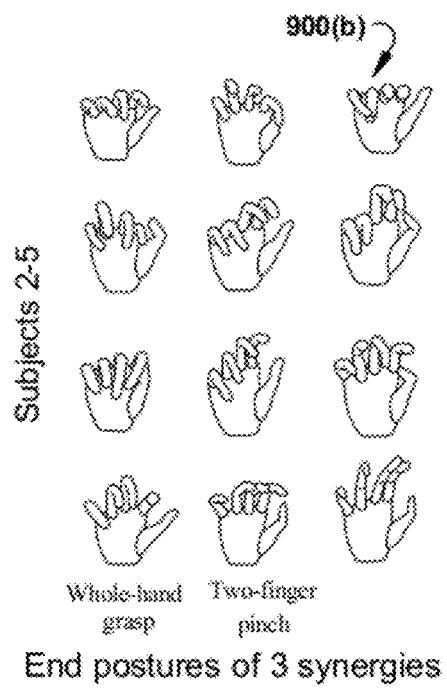

The temporal evolution of postural synergies 900(a) of Subject 1 is shown in FIG. 9(a). Each row corresponds to the temporal profile of one synergy. Each posture 902(a) is a snapshot taken at discrete time steps 904(a) of 25%, 50%, 75%, and 100% of a task time. The end posture 906(a) of synergy 1 corresponds to a whole-hand grasp (SI=0.95) and an end posture 908(a) of synergy 2 corresponds to a two finger pinch (SI=0.99). FIG. 9(b) shows the postural synergies 900(b) of subjects 2-5. Each row corresponds to the end postures of three significant synergies for one subject. The first and second columns illustrate whole-hand grasp (SIs=0.97, 0.94, 0.99, 0.90, for Subjects 2-5 respectively) and two-finger pinch synergies (SIs=0.95, 0.92, 0.93, 0.92) observed across the subjects.

Figure 10:
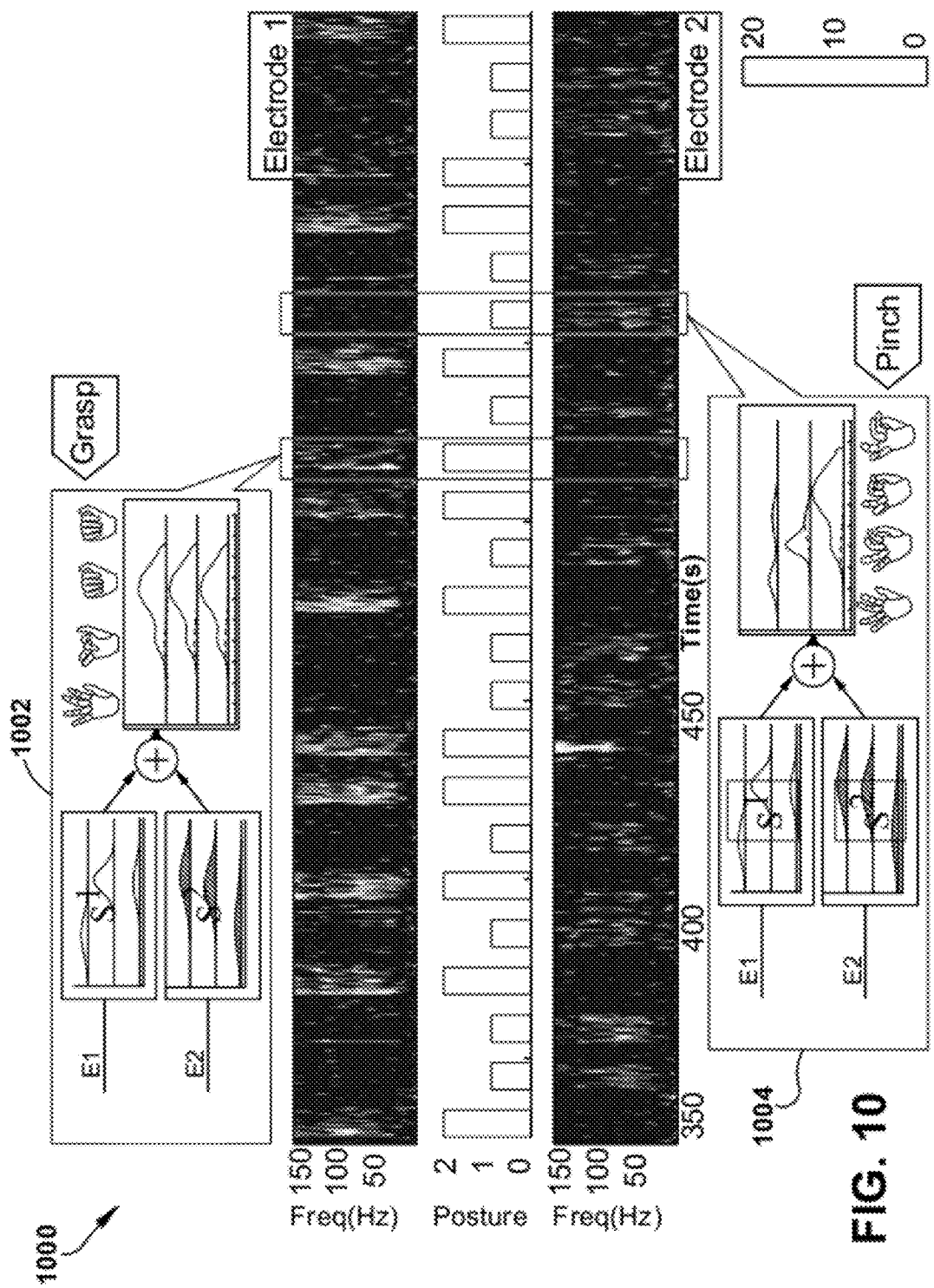
FIG. 10 is an example spectrogram illustrating synergies controlled by spectral power averaged over a high frequency band of the control signals extracted from the brain in accordance with the innovation.

During real-time control, the subject was instructed to control the whole-hand grasp and the two-finger pinch synergies by selectively modulating the activity of two selected electrodes, one located over hand motor cortical areas (grasp) and the other located over speech cortical areas (pinch). The subject modulated the selected electrodes by overt hand flexion and overt vocalization during training and testing sessions. An initial calibration process was used to determine a threshold value for each control signal $c_1$, $c_2$. The process included alternating periods of rest and movement or vocalization during the modulation of high frequency band power. The thresholds were set to the midpoint between spectral power during rest and movement or vocalization. When the task spectral power was below the power threshold, the command signal controlling a synergy was null resulting in a zero joint angular velocity. When the task spectral power was above the power threshold, the joint angular velocity was proportional to the power spectral difference, as shown in Formula (6) above. The subject had to increase the spectral power on the corresponding electrode to achieve a desired posture, within five seconds, with the virtual hand 202(*c*). Once the desired posture was achieved the subject was instructed to relax. The subject was given real-time visual feedback of the posture of the virtual hand 202(*c*). At the beginning of the session, congruent neural activities were observed in both electrodes when the subject was attempting to learn the mapping between task space and synergies' space. After a short learning period, the subject began to modulate the two control signals $c_1$, $c_2$ independently and achieve good control of the two synergies, synergy 1, synergy 2, to control the virtual hand 202(*c*), as shown in the spectrograms 1000 in FIG. 10. The spectrograms illustrate the percent change from baseline power of the two selected electrodes. Baseline power was computed during an initial rest period at the beginning of the session. Callout 1 1002 illustrates the formation of a whole-hand grasp when the average spectral power of the neural signal at electrode 1 is above its threshold and neural signal at electrode 2 is below its threshold. Similarly, Callout 2 1004 illustrates a two-finger pinch. Data is plotted from the second session when the subject started to gain good control of the two synergies, synergy 1, synergy 2.

The results of the sessions were quantified to measure the success rate of the sessions. Specifically, a session was deemed successful when only one electrode, the one corresponding to the control signal for that synergy, was modulated. A session was deemed a failure when either the non-corresponding electrode was modulated, thus forming a posture different from the desired posture, or when both electrodes were simultaneously modulated, or when neither electrodes were modulated, thus not moving the hand. The virtual hand posture itself was not used to determine success because in the case of whole-hand grasp target, simultaneously modulating both electrodes would still result in a whole-hand grasp of the virtual hand. The duration of recording sessions depended on the subject's clinical condition, willingness to participate, and the schedule of clinical procedures. Because the subject was naive to the task prior to the sessions, the training time required before the first session was longer than the training time prior to the second session. Specifically, the first training time was 750 seconds and the second training time was 250 seconds. As a result, the first session lasted for 1170 seconds and the subject was successful in 34/37 (91.9%) trials. On the other hand, the second session lasted for 625 seconds and the subject was successful in 30/31 (96.8%) trials.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

Figure 11:
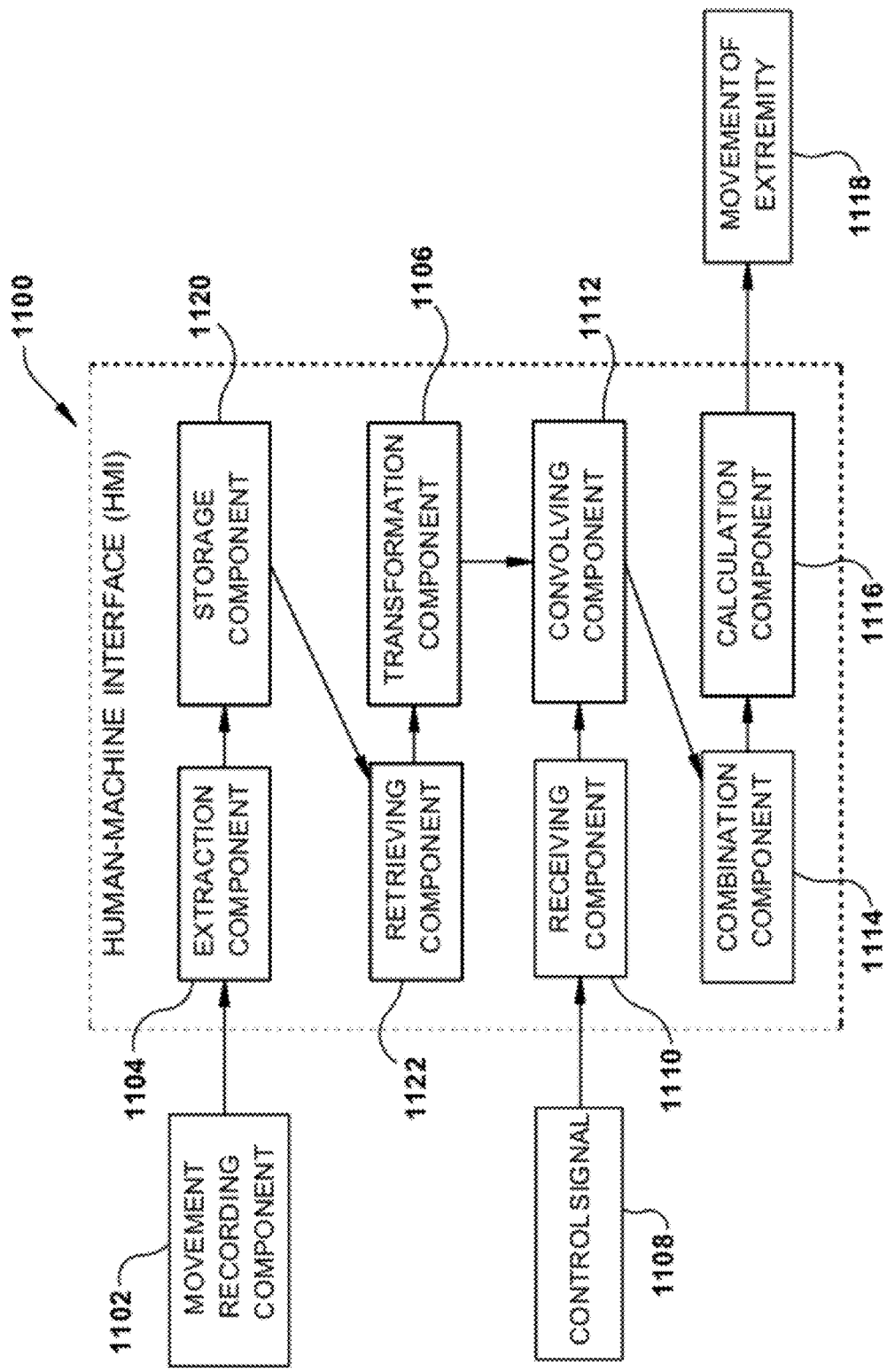
FIG. 11 is an example embodiment of a BMI system in accordance with the innovation.
Figure 12:
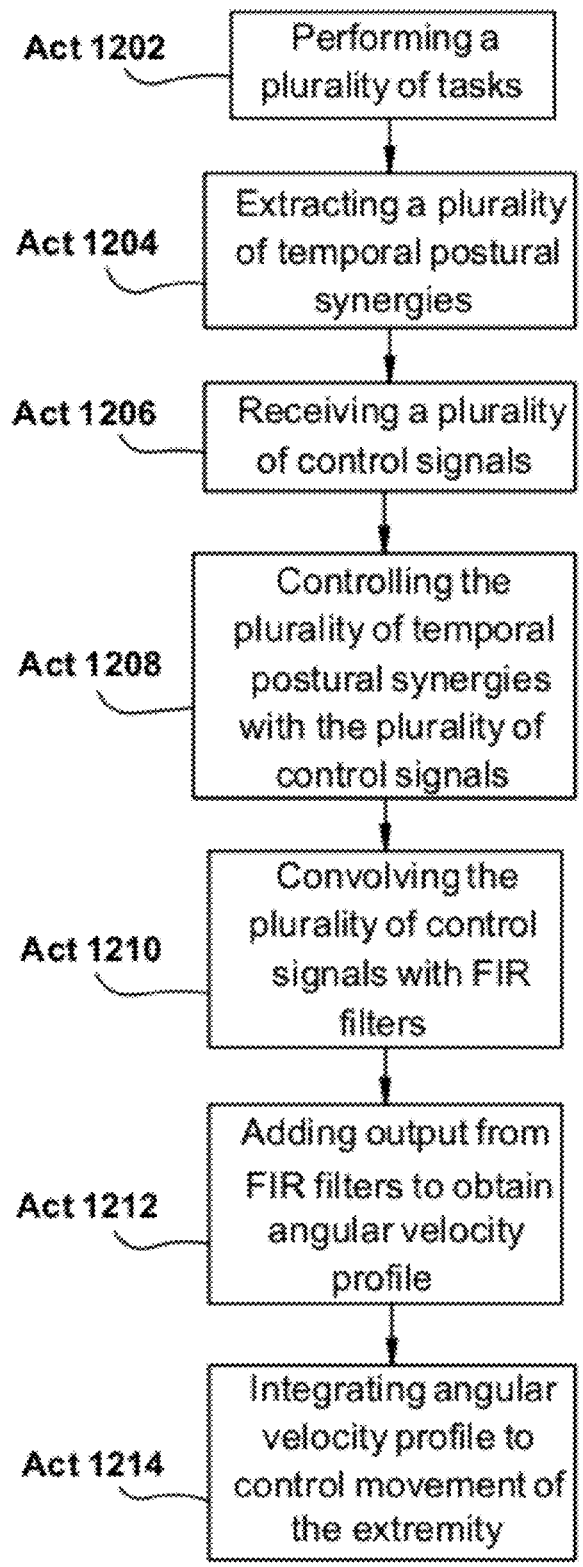
FIG. 12 is an example illustration of an example process of moving an extremity in accordance with the innovation.

FIGS. 11 and 12 illustrate an example embodiment of an HMI system that includes a BMI 1100 and an example process of controlling movement of an extremity as described above respectively implementing the innovation is illustrated. At Act 1202, the subjects perform a plurality of tasks as described above using a movement recording component 1102, such as the cyber glove 202(*c*). At Act 1204, a plurality of kinematic synergies are extracted with an extraction component 1104. The plurality of kinematic synergies are extracted from angular velocities of a plurality of joints based on the performance of the tasks. At Act 1206, a transformation component 1106 transforms the kinematic synergies into temporal postural synergies. A plurality of control signals 1106 are sent to the BMI 1100, which is generated by a subject having neurological disorders. At Act 1208, a receiving component 1110 receives the plurality of control signals 1106 and sends the control signals 1108 to a convolving component 1112. The control signals 1108 activate or control the plurality of temporal postural synergies, as described above, Act 1210. At Act 1212, the convolving component 1112 convolves the plurality of control signals 1108 and the temporal postural synergies. At Act 1214, a combination component 1114 combines or adds output responses from the convolving component 1112 to obtain a resultant angular velocity profile. At Act 1216, a calculating component integrates the resultant angular velocity profile to control the movement of the extremity.

Figure 13:
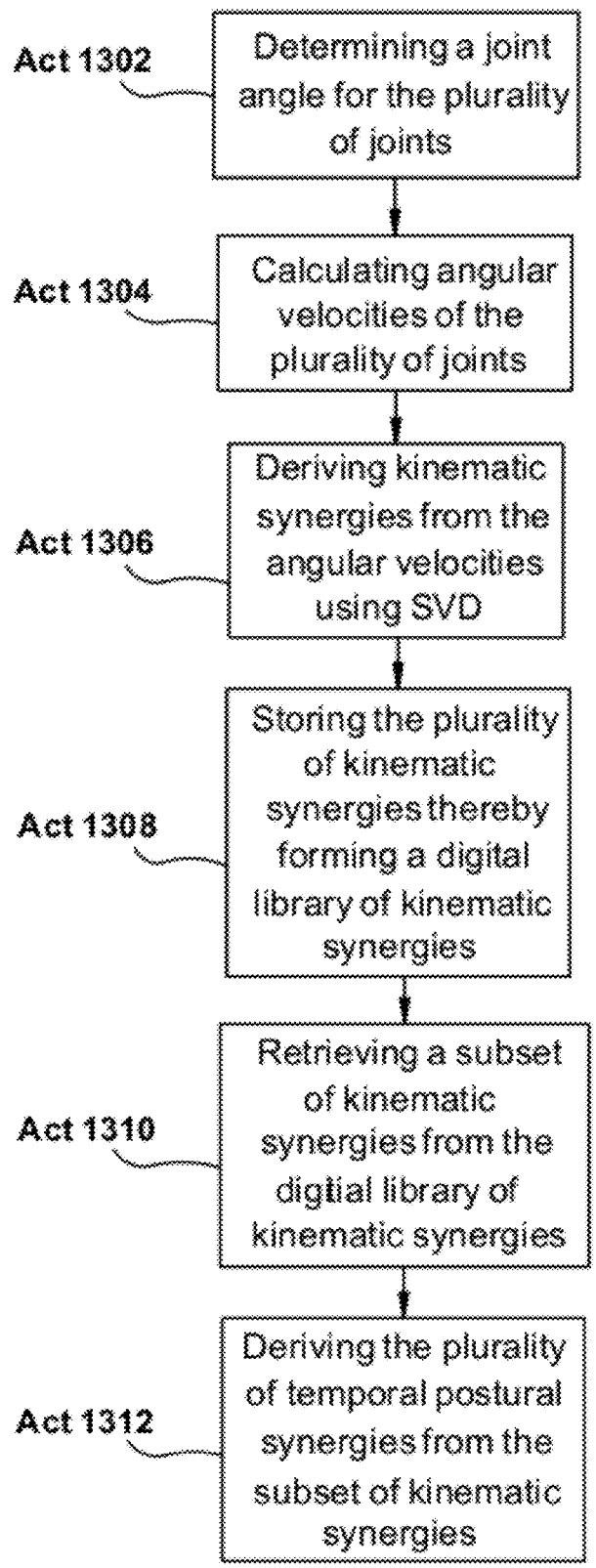
FIG. 13 is an example illustration of an example process showing an extraction of synergies in accordance with the innovation.

Referring to FIG. 13, the method of extracting the temporal postural synergies is described. At Act 1302, a joint angle for each of the plurality of joints is determined based on a result of the plurality of tasks. At Act 1304, the angular velocities of the plurality of joints are calculated based on the joint angles. At Act 1306, the kinematic synergies are derived from the angular velocities using linear and/or nonlinear dimensionality reduction methods such as, but not limited to, the SVD method and the GDM. At Act 1308, the kinematic synergies are stored in a storage component 1120 of the HMI system 1100 thereby forming a digital library of kinematic synergies. At Act 1310, a retrieving component 1122 retrieves a subset of kinematic synergies from the digital library of kinematic synergies. At Act 1312, the temporal postural synergies are derived from the kinematic synergies by integrating angular velocity profiles of the kinematic synergies.

As mentioned above, two numerical methods are used in extracting synchronous and asynchronous synergies. The gradient descent method used recursive error minimization, while the SVD method used the most commonly used eigenvectors (that corresponded to higher eigenvalues) to extract synergies. It is unknown if the synergies are recruited synchronously or asynchronously during natural movements, thus, in the innovation disclosed herein, the synergies were extracted using both methods. If the synergies are recruited synchronously, then both methods would extract the same set of synergies because the synchronous synergies model is a subset of the asynchronous synergies model.

In the innovation disclosed herein, it was observed that both methods led to similar temporal postural synergies, see FIGS. 7 and 9, which may suggest that synergies are recruited synchronously in the natural grasping movements that were tested. This is validated by comparing the end postures of the first two synergies obtained by both methods for all five subjects. Similarity indices above 0.90 were obtained for all subjects. Further, in additional tests that included 10 subjects, over 100 natural grasping movements demonstrated that major synergies that contributed significantly to the reconstruction of the movements, were recruited synchronously. This suggests that synchronous synergies can be extracted from natural grasp movements using the SVD method, which only requires a few minutes of processing time. In order to generalize other movements, it may be necessary to extract asynchronous synergies using the gradient descent method at the cost of longer processing times. The real-time model is capable of handling both synchronous and asynchronous synergies. The timing of the neural command signals ($c_{jk}$) decides whether the synergies will be used synchronously or asynchronously.

In the innovation disclosed herein, it was demonstrated that two independent neural signals $c_1$, $c_2$ control two synergies, synergy 2 and synergy 1 respectively. The use of the two neural signals $c_1$, $c_2$ achieves coordinated control of ten joints of a virtual hand in order to grasp or pinch virtual objects. One goal of the innovation is to control the synergies separately, which is essentially equivalent to two-dimensional control. The advantages of the synergy model are better realized when subjects can simultaneously control the two synergies in weighted combinations to achieve various hand postures. The two synergies controlled by the neural signals can thus be combined to achieve multidimensional control. This is crucial for controlling dexterous prosthetic limbs that are currently being developed since the number of control signals will always be limited.

The results shown herein indicate simultaneous control of two synergies to achieve multidimensional control. Simultaneous and graded control of neural signals from two different brain areas may prove challenging for subjects. Instead, decoding the native motor intent or decoding the type of grasp from neural signals in real-time and using them to command the synergies will achieve intuitive control. Through sufficient training the subjects will be able to overcome this challenge and modulate the neural signals to control synergies. The synergy model disclosed herein is not limited to electrocorticographic brain control. The synergies can potentially be controlled by neural signals extracted from noninvasive techniques like electroencephalography and magnetoencephalography or other types of control such as, limb kinematics, myoelectric control of a multidimensional prosthesis, etc.

One improvement to the real-time Human-Machine Interface Models is that the innovation demonstrates control of kinematic synergies in a real-time HMI. This is a first step toward demonstrating the potential use of time-varying kinematic synergies to achieve high-dimensional control.

Additional yet to be determined benefits may include: 1) Two synergies (whole-hand grasp and two-finger pinch) inspired by the extracted synergies were used in the real-time synergy model. Although the extracted synergies were not used in the real-time model, the Gaussian filter based synergies, nevertheless, were inspired by the extraction methods. The use of banks of Gaussian filters 504, 506 was a first approximation assuming smooth bell-shaped velocity profiles. The Gaussian filters 504, 506 are adapted for at least three reasons: 1) it is likely more difficult to control and track hand posture if synergies with multiple sub-movements are used during initial learning; 2) it simplifies the subject's transformation from task space to synergy space; and 3) Gaussian filter synergies are not subject-specific (i.e, they can be generalized across multiple users) yet they are inspired by anatomical synergies.

Gaussian filter based synergies were optimized for reconstruction using the methods described above. Using banks of Gaussian filters as synergies may limit the number of postures and the accuracy of postures that can be achieved by combining them in weighted combinations. On the other hand, extracted synergies with complex sub-movements can pose limitations on subject training as described above. Considering both limitations, it is desirable to begin subject training with Gaussian filter based synergies. As the subject learns to control these simple synergies, the complex extracted synergies can be introduced to enable more movements. The use of Gaussian filter based synergies is only a preliminary demonstration of what the real-time synergy model is capable of. This model can also include real-time control of extracted synergies.

2) Increasing the number of synergies used in real-time can possibly expand the applicability of the model. A limitation to this is the number of independent channels that can be obtained from current BMI technology. This limitation could possibly be overcome with training or neural interfacing technologies. Specifically, neural plasticity can be induced through closed-loop training. It has been demonstrated to induce plasticity to de-correlate two control signals extracted from brain areas that were originally correlated to each other. In neural interfacing technologies, high density grids such as micro-ECoG are being used in BMIs that enable more independent signals (less coherent) to be extracted. This offers potential for improved spatial resolution and increase in the number of DoF that can be controlled.

3) Currently the synergy model relies completely on the visual feedback for users to modulate the weights of synergies to successfully perform a grasp. Providing somatosensory feedback may assist the subjects in determining effective control of synergies.

4) The synergy model is purely kinematic in nature, providing joint velocity/position control. The model does not include musculoskeletal dynamics. Exporting the model into musculoskeletal modeling software can provide a simulation environment close to the real world.

5) If synergies have direct representations in neural signals then intuitive control can be achieved.

Synergies have been generalized as movement primitives that can be found across a variety of hand movements. In contrast, the innovation disclosed herein found that the synergies are task-specific. This does not mean that there are specific synergies in each grasping task. The task here means context; like reaching and grasping, hand writing, etc. The synergies specific to reaching and grasping tasks need not be used in hand writing tasks. The task-specific nature of the synergies was observed when an experiment was conducted in which the synergies extracted from grasping and pinching movements were used to reconstruct American Sign Language (ASL) postures. Reconstruction errors were larger for ASL hand posture tasks when compared to those of pinch and grasp tasks, suggesting task-specific nature of synergies. Instead of generalizing synergies across a variety of tasks, it is more effective to use task-specific synergies. Thus there will be task-specific libraries that contain task-specific synergies. For example, reaching and grasping would likely require a library that is distinct from a keyboard typing related synergy library. Thus according to application, the BMI user can learn to select the appropriate libraries. Given the limitation of the number of control signals available for a BMI, grouping the synergies into task specific libraries decreases the number of synergies that are controlled simultaneously. The selection of the libraries can be done by peripheral sensors as described above. If the type of task or motor intent can be decoded from neural signals, then decoded neural signals can select libraries.

ECoG provides a good balance between low resolution (spatial and temporal) noninvasive technologies and high resolution single neuron recordings and, thus has proved to be a promising neural recording methodology. In a recent study, it was found that both epidural and subdural recordings offer similar signal resolution, suggesting the possibility of recording high-fidelity ECoG signals epidurally and reducing the invasiveness of the procedure required to implant ECoG electrodes. During self-paced finger flexion movements, movements of different fingers elicited distinct patterns of activity on individual electrodes. Robust 2-D control using ECoG has been demonstrated in both nonhuman primates and humans. It is to be appreciated that is has been shown that ECoG has detailed neural representations in decoding finger movements during offline analysis. Within the limited recording time in the epilepsy monitoring unit, a subject was able to learn to control a synergy-based BMI. Furthermore, in a subsequent recording session, the subject was able to achieve good control in less training time when compared to the first session. Through multiple training sessions it is foreseeable that the subjects could achieve efficient control of more synergies, thus enabling multidimensional control of a virtual hand. Combining the advantages offered by ECoG and synergies, robust control of a virtual hand with high DoF, can be achieved.

In the innovation, synchronous and asynchronous temporal postural synergies were extracted using the SVD method and the gradient descent method from tasks similar to activities of daily living. Two synergies inspired by the extracted synergies to demonstrate control of a 10 DoF virtual hand with two neural command signals, thus combining the synergy model and an electrocorticographic BMI. As a result, brain control of synergies could have potential applications in controlling FES systems or dexterous prosthetic limbs.

While many of the examples of the specification and appendices are related to hand movements (e.g., hand prosthesis), it is to be understood that the features, functions and benefits of the innovation can be applied to other extremities and/or joints without departing from the scope of this specification (and attached/incorporated materials).

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of controlling movement of an extremity of a primate, robot, or machine, wherein the extremity comprises a controlled plurality of joints, comprising:

recording a plurality of tasks performed by a model subject via a movement recording component having a model plurality of joints;

extracting a plurality of temporal postural synergies from angular velocities of the model plurality of joints based on the performance of the plurality of tasks, wherein the plurality of temporal postural synergies comprises common movement primitives associated with the plurality of tasks;

receiving a plurality of control signals from a controlling subject with a neurological disorder;

controlling a subset of the plurality of temporal postural synergies with the plurality of control signals, wherein the plurality of control signals comprises one or more of a neurological signal, a muscular signal, or a signal received via a peripheral sensor; and controlling the movement of the extremity via calculating positions of the controlled plurality of joints, wherein calculating positions of the controlled plurality of joints comprises a processor performing the following steps:

convolving a subset of the plurality of control signals and the subset of temporal postural synergies with a plurality of finite impulse filters;

adding an output response from the plurality of finite impulse filters that obtains a resultant angular velocity profile; and integrating the resultant angular velocity profile to obtain the calculated positions of the controlled plurality of joints.

2. The method of claim 1, wherein extracting a plurality of temporal postural synergies from angular velocities of the model plurality of joints based on the performance of the plurality of tasks comprises:

determining a joint angle for each of the model plurality of joints based on a result of the plurality of tasks;

calculating the angular velocities of the model plurality of joints based on the joint angle;

deriving a plurality of kinematic synergies from the angular velocities; and deriving the plurality of temporal postural synergies from a subset of kinematic synergies from a digital library by integrating angular velocity profiles of the subset of kinematic synergies.

3. The method of claim 2, wherein prior to deriving the plurality of temporal postural synergies from a subset of kinematic synergies by integrating angular velocity profiles of the subset of kinematic synergies, the method further comprises:

forming the digital library of kinematic synergies by storing the plurality of kinematic synergies; and retrieving the subset of kinematic synergies from the digital library of kinematic synergies.

4. The method of claim 3, wherein the plurality of kinematic synergies are derived using linear and/or non-linear dimensionality reduction methods.

5. The method of claim 1, wherein the plurality of temporal postural synergies are synchronous synergies and are extracted from the model subjects, the model subjects having no neurological disorders.

6. The method of claim 5, wherein the angular velocity profile of the movement of the extremity is a weighted linear combination of the synchronous synergies extracted from recordings where impulses of the synchronous synergies occur at the same time.

7. The method of claim 6, wherein the control signals are invasive or non-invasive brain signals and/or muscular signals and/or signals detected by peripheral sensors.

8. The method of claim 7, wherein extracting a plurality of temporal postural synergies from angular velocities of a model plurality of joints based on the performance of the plurality of tasks comprises:
- determining a joint angle for each of the model plurality of joints based on a result of the plurality of tasks;
- calculating the angular velocities of the model plurality of joints based on the joint angle;
- deriving kinematic synergies from the angular velocities; and
- deriving the temporal postural synergies from a subset of kinematic synergies from a digital library by integrating angular velocity profiles of the subset kinematic synergies.

9. The method of claim 8, wherein prior to deriving the plurality of temporal postural synergies from the subset of kinematic synergies by integrating angular velocity profiles of the subset of kinematic synergies, the method further comprises:
- storing the plurality of kinematic synergies thereby forming the digital library of kinematic synergies; and
- retrieving the subset of kinematic synergies from the digital library of kinematic synergies.

10. The method of claim 9, wherein the plurality of kinematic synergies are derived using linear and/or non-linear dimensionality reduction methods.

11. The method of claim 1, wherein the plurality of temporal postural synergies are asynchronous synergies extracted from the model subjects using linear and/or nonlinear dimensionality reduction methods, the model subjects having no neurological disorders.

12. The method of claim 11, wherein the angular velocity profile of the movement of the extremity is a weighted linear combination of the asynchronous synergies extracted from recordings where impulses of the asynchronous synergies occur at different times.

13. The method of claim 12 further comprising varying a weight of the asynchronous synergy and a time shift of the asynchronous synergy according to a type of task.

14. The method of claim 13, wherein the control signals are invasive or non-invasive brain signals and/or muscular signals and/or signals detected by peripheral sensors.

* * * * *